(12) United States Patent
Childress

(10) Patent No.: US 7,699,610 B2
(45) Date of Patent: Apr. 20, 2010

(54) FLEXIBLE DENTURE AND METHOD TO MAKE SAME

(76) Inventor: Bryan Childress, 611 Firefly Catch, Springdale, AR (US) 72762

( * ) Notice: Subject to any disclaimer, the term of this patent is extended or adjusted under 35 U.S.C. 154(b) by 701 days.

(21) Appl. No.: 11/475,366

(22) Filed: Jun. 27, 2006

(65) Prior Publication Data

US 2007/0009852 A1    Jan. 11, 2007

Related U.S. Application Data

(63) Continuation-in-part of application No. 10/898,479, filed on Jul. 22, 2004, now abandoned.

(51) Int. Cl.
*A61C 13/00* (2006.01)
(52) U.S. Cl. .................. 433/167; 433/168.1; 433/171; 433/184; 433/188; 433/190; 433/197
(58) Field of Classification Search .............. 433/188, 433/184, 197, 190, 171, 168.1, 167
See application file for complete search history.

(56) References Cited

U.S. PATENT DOCUMENTS

| | | | |
|---|---|---|---|
| 2,770,880 A | 11/1956 | Sherrod | |
| 3,083,459 A | 4/1963 | McMurry et al. | |
| 3,496,936 A | 2/1970 | Gores | |
| 3,628,248 A * | 12/1971 | Kroder et al. | 433/175 |
| 3,783,514 A * | 1/1974 | Kersten | 433/171 |
| 3,813,778 A | 6/1974 | Van Handel | |
| 3,837,079 A | 9/1974 | Cecero | |
| 3,921,293 A * | 11/1975 | Keumurdji | 433/168.1 |
| 3,987,546 A | 10/1976 | Trampe | |
| 4,175,322 A | 11/1979 | Tureaud | |
| 4,370,133 A | 1/1983 | Stempel | |
| 4,376,629 A | 3/1983 | Ebeling | |
| 4,457,713 A | 7/1984 | Schneider | |
| 4,583,947 A | 4/1986 | Hazar | |
| 4,642,052 A * | 2/1987 | Carlson | 433/189 |

(Continued)

OTHER PUBLICATIONS

Technical Bulletin: Valplast, 2 pages, Dental Arts Laboratories, http://www.dentalartslab.com/images/pdf/Valplast1.pdf.

(Continued)

*Primary Examiner*—Ralph A Lewis
*Assistant Examiner*—Eric Rosen
(74) *Attorney, Agent, or Firm*—Dunlap Codding, P.C.

(57) ABSTRACT

A flexible denture is provided with a denture plate and a false teeth assembly. The denture plate includes a support member and a deformable member. The support member has an approximately U-shaped base, a labial wall and a lingual wall extending from the base, wherein the labial and lingual walls form an approximate U-shaped cross-section along an imaginary vertical plane to form a channel. The deformable member extending across the channel and spaced a distance from the U-shaped base to separate the channel into a gum receiving section and a fitting section, the fitting section including a plurality of ridges extending between the U-shaped base and the deformable member. The deformable member is constructed of soft and pliable material. The false teeth assembly includes a plurality of false teeth secured to the base, the false teeth assembly includes a reinforcing bar embedded within and connecting the plurality of false teeth.

11 Claims, 8 Drawing Sheets

U.S. PATENT DOCUMENTS

| | | | |
|---|---|---|---|
| 4,654,006 | A | 3/1987 | Kusano et al. |
| 4,764,115 | A | 8/1988 | Willits et al. |
| 4,923,795 | A | 5/1990 | Franklin |
| 4,983,334 | A | 1/1991 | Adell |
| 5,403,186 | A | 4/1995 | Ginsburg |
| 5,431,563 | A * | 7/1995 | Huybrechts .......... 433/48 |
| 5,499,633 | A | 3/1996 | Fenton |
| 5,566,684 | A | 10/1996 | Wagner |
| 5,632,621 | A | 5/1997 | Moodley |
| 5,848,898 | A * | 12/1998 | Mays et al. .......... 433/198 |
| 6,077,075 | A | 6/2000 | Bedard et al. |
| 6,491,521 | B1 | 12/2002 | Fowler, Jr. |
| 6,505,625 | B1 | 1/2003 | Uenishi |
| 2002/0144686 | A1 | 10/2002 | Cook |
| 2003/0136416 | A1 | 7/2003 | White |

OTHER PUBLICATIONS

Dydent: Dental Tours to the Philippines, 1 page, http://www.dydent.com/valplast.htm, Apr. 4, 2006.

Google Definition Search: Thermoplastic, http://www.google.com/search?hl=en&hs=2xp&lr=&client=firefox-..., Apr. 4, 2006.

Yunus et al., "Some Flexural Properties of a Nylon Denture Base Polymer", Abstract of Article from PubMed, Jan. 2005, 32(1):65-71, Journal Oral Rehabilitation, http://www.ncbi.nlm.nih.gov/entrez/query.fcgi?cmd=Retrive&db=P....

* cited by examiner

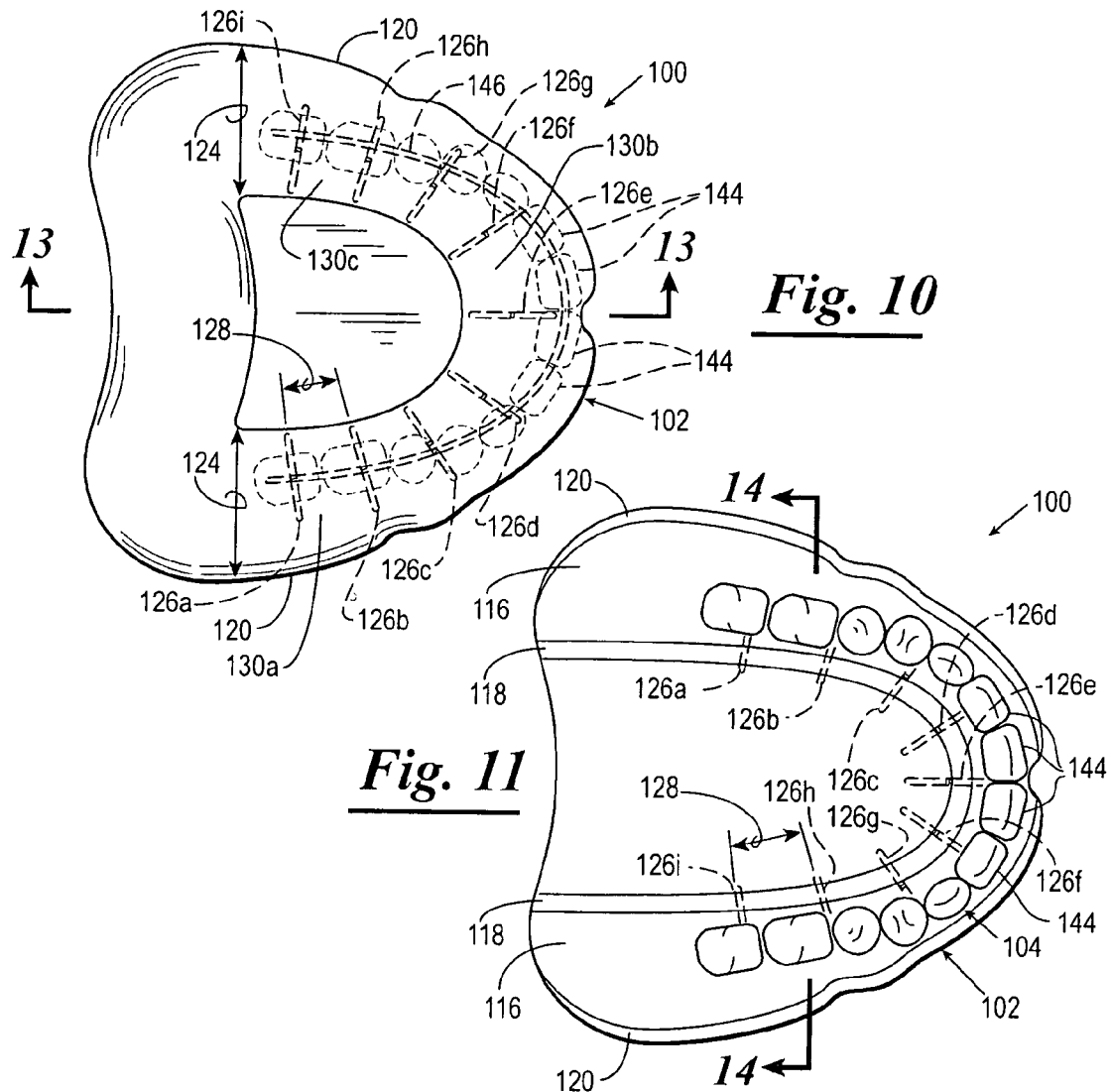
*Fig. 10*
*Fig. 11*
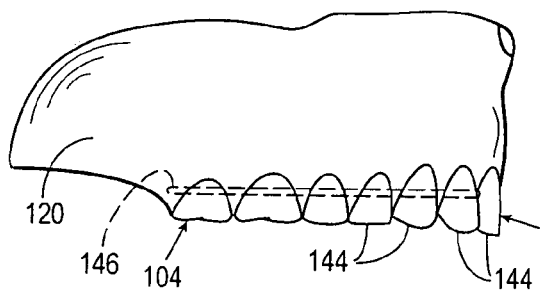
*Fig. 12*
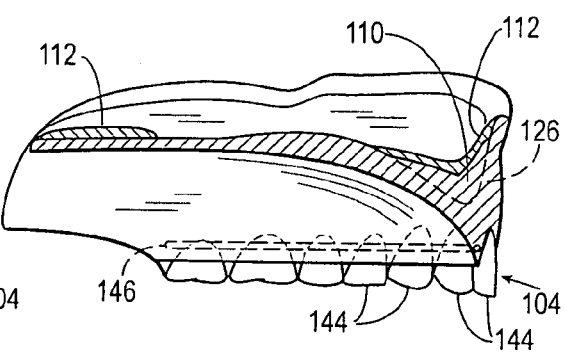
*Fig. 13*

FLEXIBLE DENTURE AND METHOD TO MAKE SAME

REFERENCE TO PENDING APPLICATIONS

The present application is a continuation-in-part of U.S. Ser. No. 10/898,479, filed Jul. 22, 2004 now abandoned the contents of which are expressly incorporated by reference herein in its entirety.

REFERENCE TO MICROFICHE APPENDIX

This application is not referenced in any microfiche appendix.

BACKGROUND OF THE INVENTION

1. Field of the Invention

The present invention relates to a denture and method to make the same. More particularly, the present invention relates to a flexible denture and a method to make the same.

2. Background

Prosthetic dentures are known in the prior art. These dentures typically include a denture plate portion and a series of artificial teeth attached to the denture plate portion. The terminology for a denture is fairly consistent, however, there are some variations. Thus, for purposes of this invention, the term denture plate refers to that portion of the denture that rests against the user's gums and receives the artificial teeth.

The conventional denture plate portion is made from a particularly hard material, such as acrylic. This material allows for the denture to have a potentially long life. The utilization of hard material, however, has its disadvantages.

The conventional denture must be manufactured in a series of steps so that pertinent information particular in an individual patient's mouth can be collected and used to evaluate progress toward the final denture product. This process requires several appointments with the dentist. For a denture wearer, this can result in great inconvenience, embarrassment and often missed work. For the dentist, the traditional method of constructing dentures often results in a large time investment representing lost income and income potential.

Additionally, the hard denture plate can come out of alignment causing discomfort to the patient. Further, due to a variety of factors, the denture may lose retention to the patient's gums. One common cause for retention failure is when pressure is applied to one side of the denture plate causing the opposing side to loose and separate from the gum line. An additional disadvantage is that due to the hardness of the denture plate, the denture has the tendency to chip, crack or break. When the denture comes out of alignment, loses retention or breaks, it may result in physical complications such as inflammation of tissues, soreness and discomfort to the patient. Further, there are additional costs and lost time by the patient and dentist associated with repairing or replacing the broken denture.

Clearly there is a need for a denture that can improve upon the prior art dentures.

SUMMARY OF THE INVENTION

The present invention satisfies the needs discussed above. The present invention is generally directed towards a denture, more particularly towards a pre-made denture having a denture plate comprising a support member and a deformable member forming adaptive zones (gum receiving section) that conforms to the contour of a user's gum.

One aspect of the present invention provides for a denture having a denture plate having an approximately U-shaped base. A U-shaped cross-section is created by the inclusion of a labial wall and a lingual wall extending from the base. The denture plate is constructed from a soft, pliable plate material. The inner portion of the U-shaped cross-section of the denture plate fits directly against the gums in the user's mouth.

The soft, pliable material forming the denture plate can be any material capable of becoming reshapable when heated, yet remain soft and pliable when cooled. Such material includes, but is not limited to, thermo-forming plastic material.

A plurality of false teeth are secured to the base portion of the denture plate. The false teeth can be made from a durable material, such as porcelain, acrylic, and an advanced engineering plastic. These teeth can be connected together with a reinforcing bar or wire. The false teeth can be bonded to the denture plate mechanically or chemically.

In another aspect of the present invention, a set of dentures, i.e. an upper denture and a lower denture is disclosed. Both the upper and lower dentures are constructed as set out above with the upper denture having an additional palate portion extending between the approximate U-shaped base. This palate portion is part of and constructed from the same material as other portions of the denture plate.

The dentures of the present invention can be made by one of two general methods. One of which is a single custom set made specifically for an individual, i.e. having the dentures made from a specific bite and other records or impressions from a specific individual. The second method is a pre-manufactured version which is made for the public in general, i.e. having the dentures made without any prior bite or the other records or impressions. Such dentures can be manufactured in different sizes and shapes. This allows for pre-making a denture prior to its fitting to a patient. Such denture would have the capability of being reshaped and be fitted to a patient at a later time. Thus, mass production of such dentures is made possible. The pre-manufactured version can be custom adapted to the patient by two (2) general means. First, indirectly be taking impressions of the patient's ridges and bit relation, creating articulating stone models, selecting the appropriate version of the pre-manufactured denture and adapting the dentures on to articulating models in the presence of heat, such as boiling water. The adaption might consist of adapting the base tightly to the stone, establishing the vertical dimension, correcting the position of the teeth, cooling, and trimming excess material). Second method is directly adapting which in many aspects is the same as the first method, but with no impressions or models. Instead adaptation is made directly onto the patient's mouth by heating and forming. This process consists of heating (e.g., in boiling water), then quenching the material by cooling, e.g., for approximately 5 seconds in cool water. The device is then placed in the mouth. The patient then closes the mouth to establish the vertical dimension and bite relation. The device is then allowed to cool, removed, and has excess material trimmed.

In another aspect of the present invention, a method of making a denture is disclosed. This method includes the steps of creating an impression of a patient's ridges then forming a mold of the impression. False teeth are then set into the mold. The upper and lower dentures can be generically formed or custom dentures can be made using commonly known compression flask techniques, the main difference being the use of soft, pliable, thermo-plastic material, instead of acrylic, for the use of the entire denture base; and the actual compression being done in a heated (e.g., boiling water) environment.

In another aspect of the method the present invention, the method described above is disclosed having the additional step of confirming the fit and bite relative to a patient's mouth by reheating and adjusting due to the thermal properties of the material, directly in the patient's mouth.

Upon reading the above description, various alternative embodiments will become obvious to those skilled in the art. These embodiments are to be considered within the scope and spirit of the subject invention, which is only to be limited by the claims which follow and their equivalents.

BRIEF DESCRIPTION OF THE DRAWINGS

FIG. 10 is a top plan view of another example of a denture constructed in accordance with the present invention.

FIG. 11 is a bottom plan view of the denture depicted in FIG. 10.

FIG. 12 is a side elevational view of the denture depicted in FIG. 10.

FIG. 13 is a cross-sectional view of the denture depicted in FIG. 10, taken along the lines 13-13 of FIG. 10.

DETAILED DESCRIPTION OF THE INVENTION

The attached drawing demonstrates an embodiment of the present invention. It is to be understood that the invention is not limited in its application to the details of the construction and arrangement of parts illustrated in the accompanying drawings. The invention is capable of other embodiments and of being practiced or carried out in a variety of ways. It is to be understood that the phraseology and terminology employed herein are for the purpose of description and not of limitation.

Figure 1:
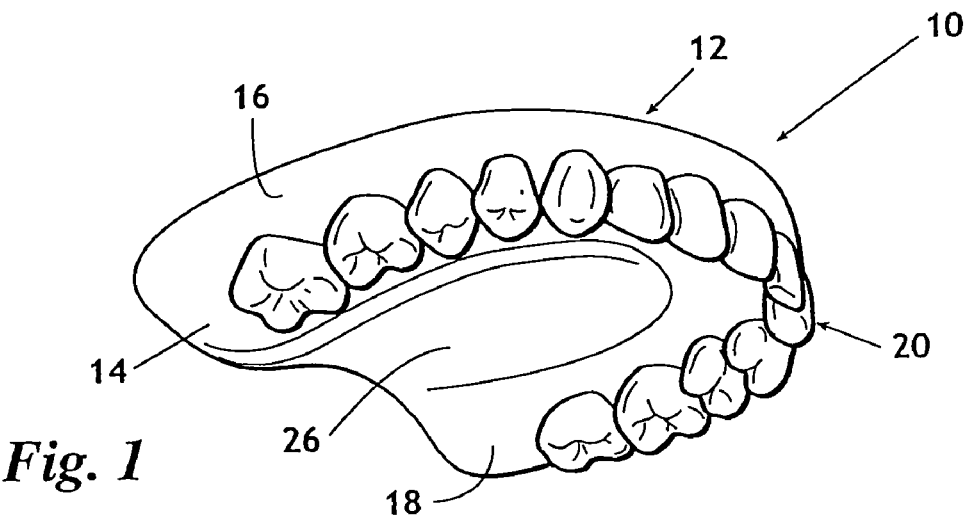
FIG. 1 is a perspective view of an embodiment of the present invention configured for the upper portion of a mouth.
Figure 9:
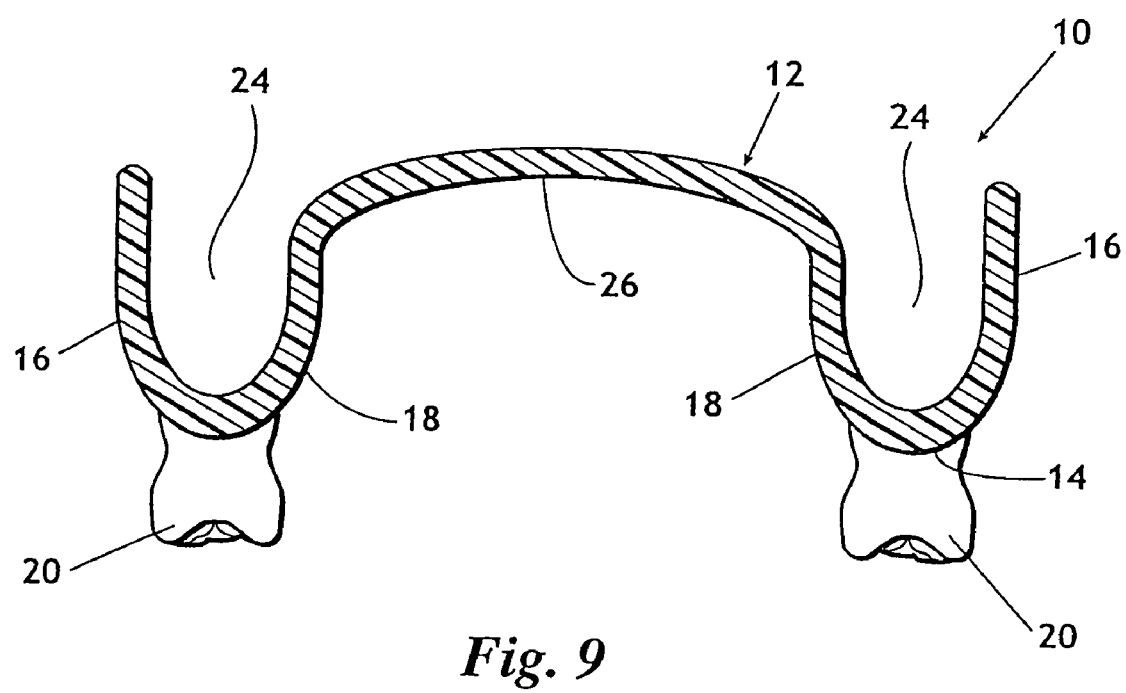
FIG. 9 is a cross-sectional view through line 9-9 of FIG. 8.

As shown in FIGS. 1 and 9, an embodiment 10 of the inventive denture is disclosed. This embodiment 10 is intended for use as an "upper" denture, i.e. a denture for use with the upper portion of a patient's mouth. Embodiment 10 comprises a denture plate 12 having a base 14 which has an approximate U-shaped as taken through an imaginary horizontal plane. Extending away from base 14 is a labial wall 16 and a lingual wall 18 forming an approximate U-shape cross-section 24 along an imaginary vertical plane. A plurality of false teeth 20 are secured to base 14 of denture plate 12. The false teeth 20 can be made from a durable material, such as porcelain and acrylic.

The denture plate 12 is constructed from a soft, pliable plate material. The inner portion of the U-shaped cross-section 24 of the denture plate fits directly against the gums (not shown) in the user's mouth. Additionally, embodiment 10 includes a palate portion 26 extending across the U-shape of base 14. Palate portion 26 is part of and made from the same material as denture plate 12.

Figure 3:
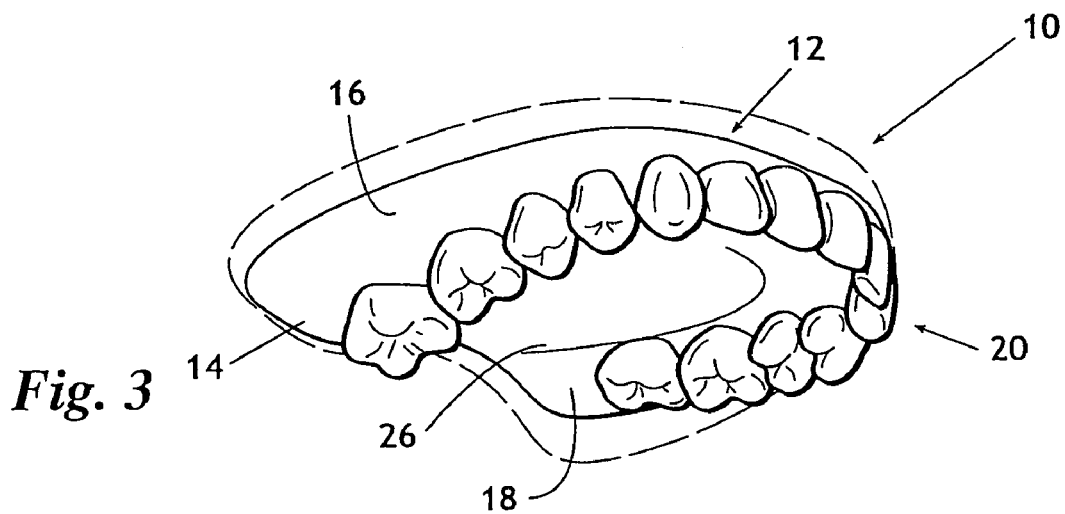
FIG. 3 is a perspective view of the embodiment of the present invention as set forth in FIG. 1 showing flexure.
Figure 4:
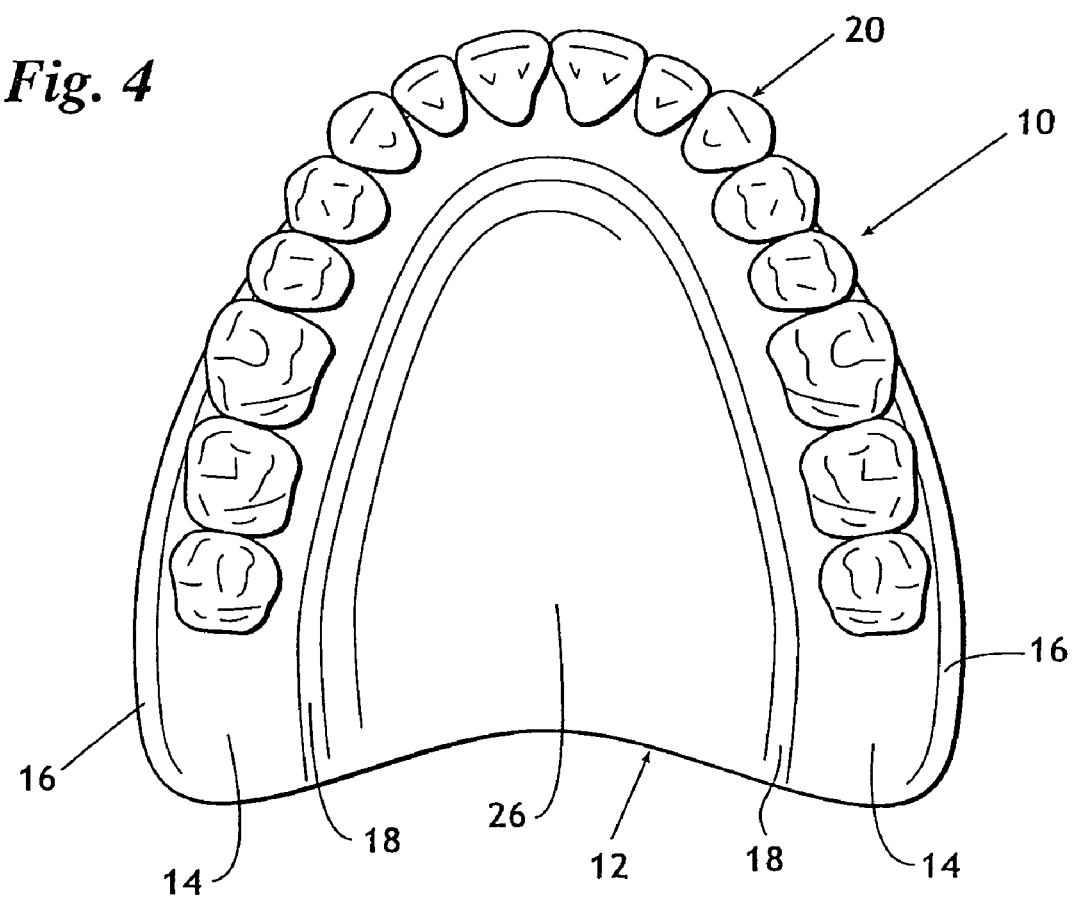
FIG. 4 is a bottom plan view of the embodiment of the present invention as set forth in FIG. 1.
Figure 6:
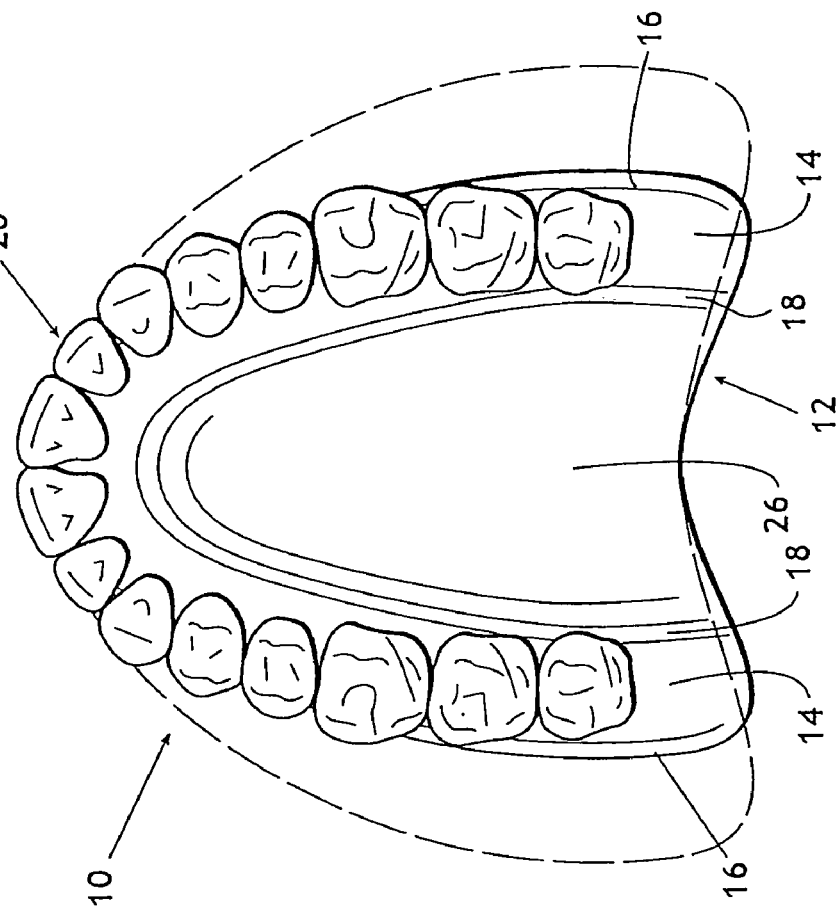
FIG. 6 is a bottom plan view of the embodiment of the present invention as set forth in FIG. 4 showing flexure.
Figure 8:
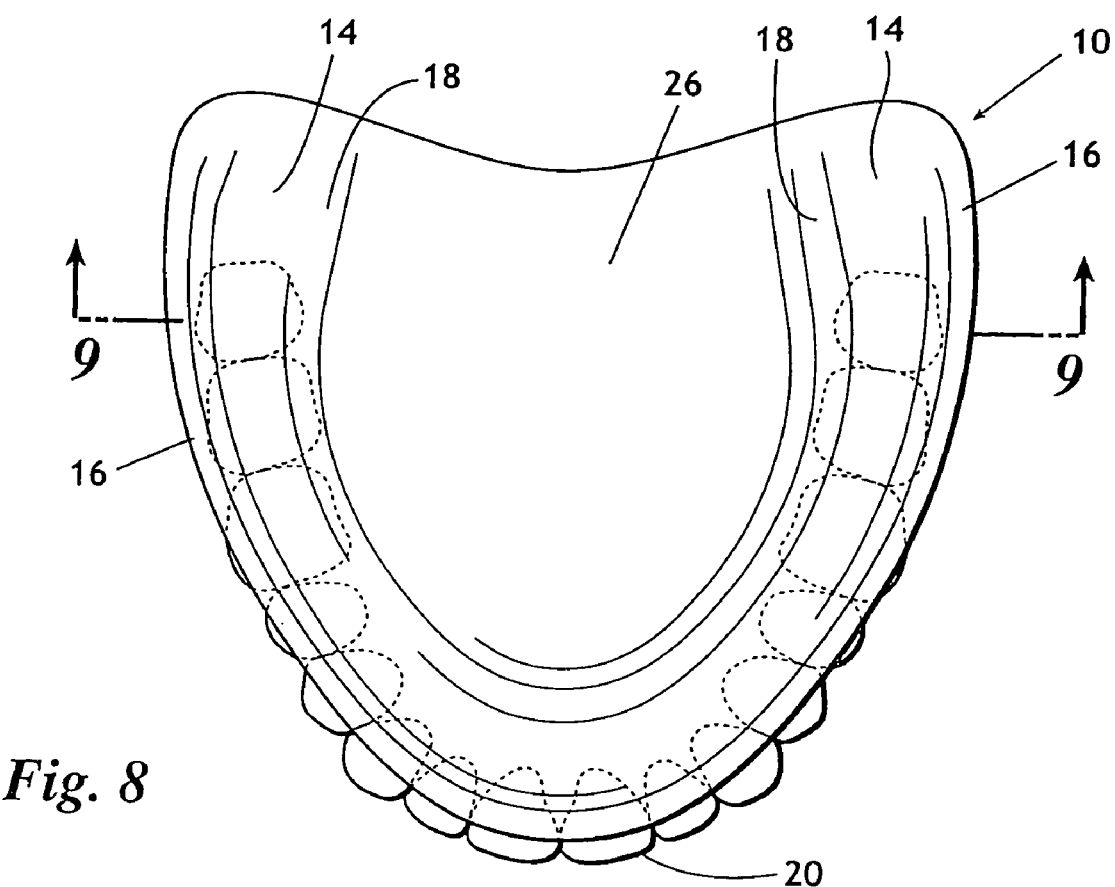
FIG. 8 is a top plan view of the embodiment of the present invention as set forth in FIG. 1.

The soft, pliable plate material can be any material capable of being reshaped when heated, yet remains soft and pliable when cooled. Such material includes, but is not limited to, thermo-forming plastic material. The pliability of the embodiment 10 is shown in FIG. 3 and FIG. 6.

In operation, this embodiment of the present invention can be created for a specific person. It is created by first creating an impression of a patient's teeth. A mold of the impression is formed. Standard, well-known processes for creating this mold can be used and are within the scope of the present invention.

False teeth are then set into the mold. Base material which is capable of becoming pliable when heated is then heated into such pliable state. One such base material can be a soft, pliable thermo-forming plastic material.

The heated base material is then placed into the mold. The heated base material and false teeth are then compressed to join the teeth to the heated base material. This compression can be conducted using a heated substance, such as, in boiling, or near boiling, water. After the base material and false teeth are compressed, they are cooled and any excess material is trimmed. The fit and bite relative to the patient's mouth can be conformed prior to heating the base material into a pliable state.

Additionally and by way of example, stereolithography could be employed in a situation where a custom "upper" denture 100 and "lower" denture 200 are desired. An impression would be taken of the patient's mouth. The impression would be used to form a model of the mouth. The impression could then be laser scanned resulting in a 3-D Computer Aided Design (CAD) model. The CAD model for the custom base set could then be manipulated by a variety of means to result in a computer model suitable to work from to create physical components. Also, denture plates 12 could be created in 3-dimensional CAD software. The ultimate result of the CAD modeling process would be a file that could be used to create physical models by processes such as precision machining or stereolithography.

In the case of stereolithography, the resulting model might be of the mold used to create a patient's custom "upper" denture 100 and "lower" denture 200. Then, when the stereolithography apparatus (SLA) model is complete, it is used as a sacrificial item to create denture plates 12 from suitable materials.

The stereolithography (or SLA) process is simply an example of the many types of rapid manufacturing or rapid prototyping methods. Other examples include, but are not limited to, Selective Laser Sintering (SLS), wax printing, and fused deposition modeling (FDM).

Additionally, this embodiment can be created for a generic user. This is done be creating a denture with a general mold, and not a specific mold of a patient's teeth. This allows the general denture to be form fitted to the user's mouth without the need for multiple appointments with the dentist.

Further, by using pliable material, the denture is capable of flexure, as shown in FIGS. 3 and 6. This flexure allows for a better management of the pressure asserted on the denture by the user, which in turn creates better retention to a patient's gums. Further, by being flexible, the denture is not subject to the same disadvantages of chipping and cracking as the prior art dentures. Thus, this embodiment reduces the occurrences of physical complications such as inflammation of tissues, soreness and discomfort to the patient. Another advantage of the use of the pliable material is the reduction in cost and time by the patient and dentist associated with the creation, repairing and/or replacing broken dentures.

Figure 2:
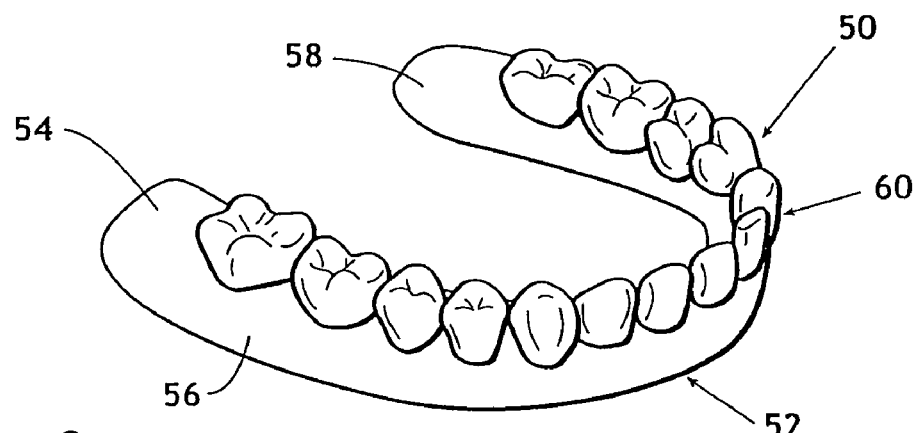
FIG. 2 is a perspective view of an embodiment of the present invention configured for the lower portion of a mouth.
Figure 5:
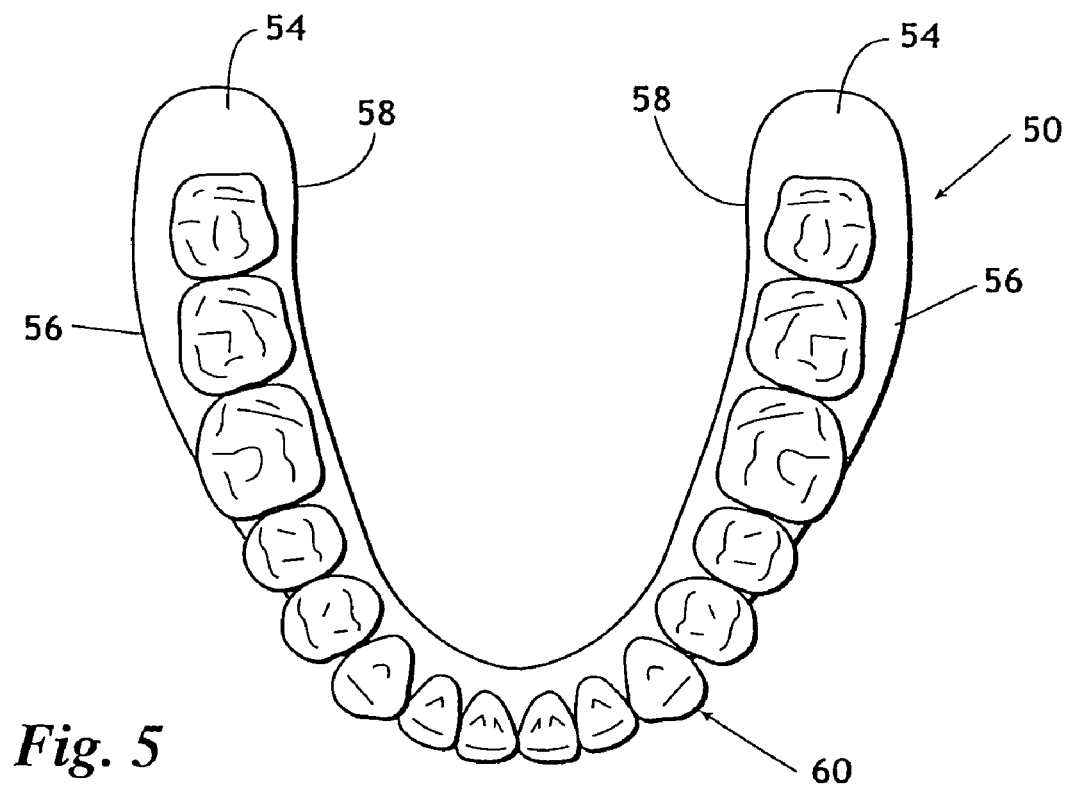
FIG. 5 is a top plan view of the embodiment of the present invention as set forth in FIG. 2.
Figure 7:
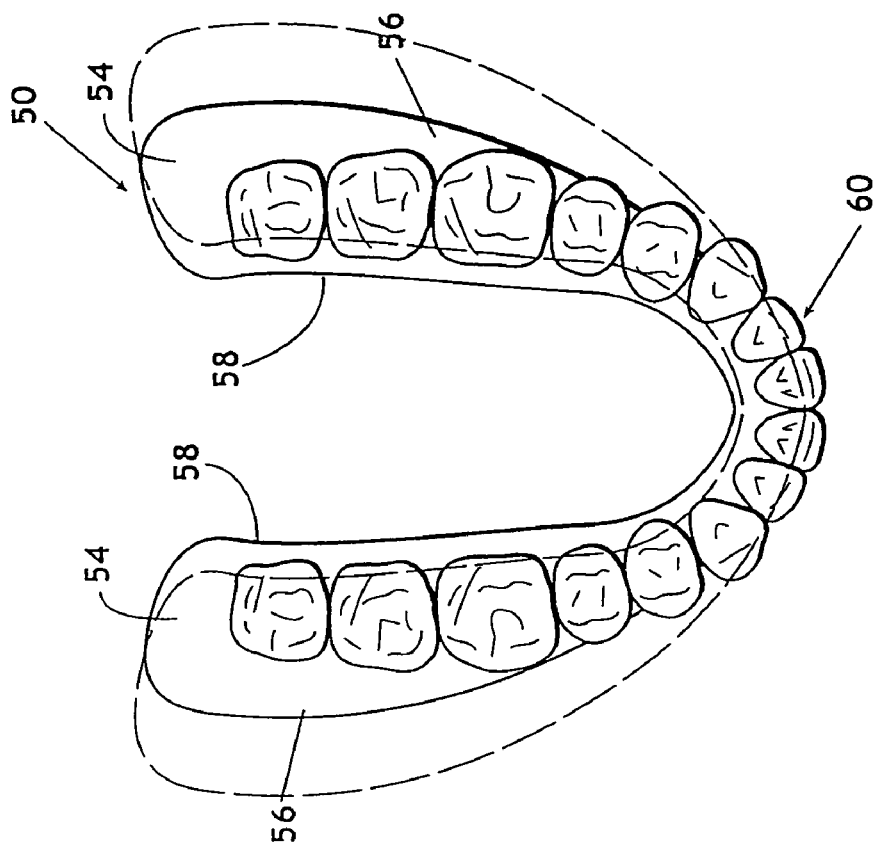
FIG. 7 is a top plan view of the embodiment of the present invention as set forth in FIG. 5 showing flexure.

Another embodiment 50 of the present invention, as shown in FIGS. 2 and 5, is disclosed. This embodiment 50 is intended for use as a "lower" denture, i.e. a denture for use with the lower portion of a patient's mouth. This embodiment 50 is similar to embodiment 10 shown above, in that it comprises denture plate 52 having a base 54 which has an approximate U-shape as taken through an imaginary horizontal plane. Further, extending away from base 54 is a labial wall 56 and a lingual wall 58 forming an approximate U-shape cross-section 54 along an imaginary vertical plane. A plurality of false teeth 60 are secured to base 54 of denture plate 52. The false teeth 60 can be made from a durable material, such as porcelain or acrylic.

The denture plate 52 is constructed from a soft, pliable plate material. The inner portion of the U-shaped cross-section 54 of the denture plate fits directly against the gums (not shown) in the user's mouth. However, embodiment 50 does not include a palate portion extending across the U-shape of base 14. Embodiment 50 is made from the same type of soft, pliable plate material as set forth with embodiment 10.

Referring now to FIGS. 10-14, shown therein and designated by reference numeral 100 is another example of a denture constructed in accordance with the present invention. In general, the denture 100 is provided with a denture plate 102, and a false teeth assembly 104 (FIG. 11). The denture plate 102 is provided with a support member 110 (FIG. 13), and a deformable member 112 (FIG. 13). As will be discussed in more detail below, the support member 110 and the deformable member 112 are preferably both constructed of soft and pliable materials, such as thermo-forming materials characterized as ethyl vinyl acetates. However, it should be understood that other materials may be used in accordance with the present invention. The support member 110 is preferably constructed of a material which is firmer than the material from which the deformable member 112 is constructed. In general, the deformable member 112 is constructed so as to be reshaped to fit against a patient's gums. The support member 110 is preferably constructed of a firmer soft and pliable material so as to support the false teeth assembly 104 and to substantially prevent the false teeth assembly 104 from moving while the patient is chewing.

In general, the support member 110 is provided with a base 116, a lingual wall 118, and a labial wall 120. When the denture 100 is configured as an upper denture as shown in FIGS. 10-14, the support member 110 can also be provided with a palate portion 122.

The denture 100, is intended for use as an upper denture in a similar manner as the embodiment 10 described above with respect to FIG. 1. As is well known in the art, the upper denture is for use with the upper portion of a patient's mouth. The denture plate 102 is provided with an approximate U-shape as taken through an imaginary horizontal plane. The base 116, the lingual wall 118, and the labial wall 120 cooperate to form a channel 124, which has an approximate U-shaped cross-section. It should be understood that the term "base" as used herein is part of the support member 110 which connects the support member 110 to the false teeth assembly 104, and also serves to separate the lingual and labial walls 118 and 120 so that the base 116, the lingual wall 118, and the labial wall 120 form the channel 124.

The support member 110 is also provided with a plurality of ridges 126 which extend across and are spatially disposed in the channel 124. In the example depicted in FIG. 10, ten of the ridges 126 are shown and designated for purposes of clarity with the reference numerals 126a, 126b, 120c, 126d, 126e, 126f, 126g, 126h, and 126i. It should be understood that although ten of the ridges 126 are depicted in FIG. 10, the support member 110 can be provided with more or less of the ridges 126. Each of the ridges 126 preferably extend approximately transversely across the channel 124, and are spatially disposed along the length of the channel 124. Thus, for example, as best shown in FIG. 10 the ridge 126a is spaced a distance 128 from the ridge 126b so as to form a gap 130 there between. In a similar manner, all of the ridges 126 are spatially disposed from an adjacently positioned ridge 126 so as to form the gaps 130 there between. It should be understood that only three of the gaps 130 are labeled in FIG. 10 and designated by the reference numerals 130a, 130b, and 130c for purposes of clarity. Although the ridges 126 are shown in FIG. 10 as extending generally at right angles to the direction of the channel 124 in which such ridges 126 are positioned, it should be understood that the ridges 126 can extend at essentially any angle with respect to the direction of the channel 124 in which such ridge 126 is positioned, so long as the ridges function as described herein.

The ridges 126 are constructed of a deformable material which is capable of being reshaped to fit to the patient's gums upon fitting of the denture 100 to the gum of the patient, and also to retain the reshaped form so that the denture 100 remains fitted to the patient's gum. Preferably, the ridges 126 are integrally formed with the base 116, lingual wall 118, and the labial wall 120 of the support member 110. However, it should be understood that the ridges 126, the base 116, the lingual wall 118, and the labial wall 120 can be separately constructed and then connected to form the support member 110. Further, the support member 110 is preferably constructed of a single material to form the base 116, lingual wall 118, labial wall 120, and the ridges 126. However, the present invention also contemplates the support member 110 being constructed of one or more different types of materials. Thus, for example, the ridges 126 could be formed of a different type of material than that used to form the base 116, lingual wall 118, labial wall 120, and/or the palate portion 122.

Figure 14:
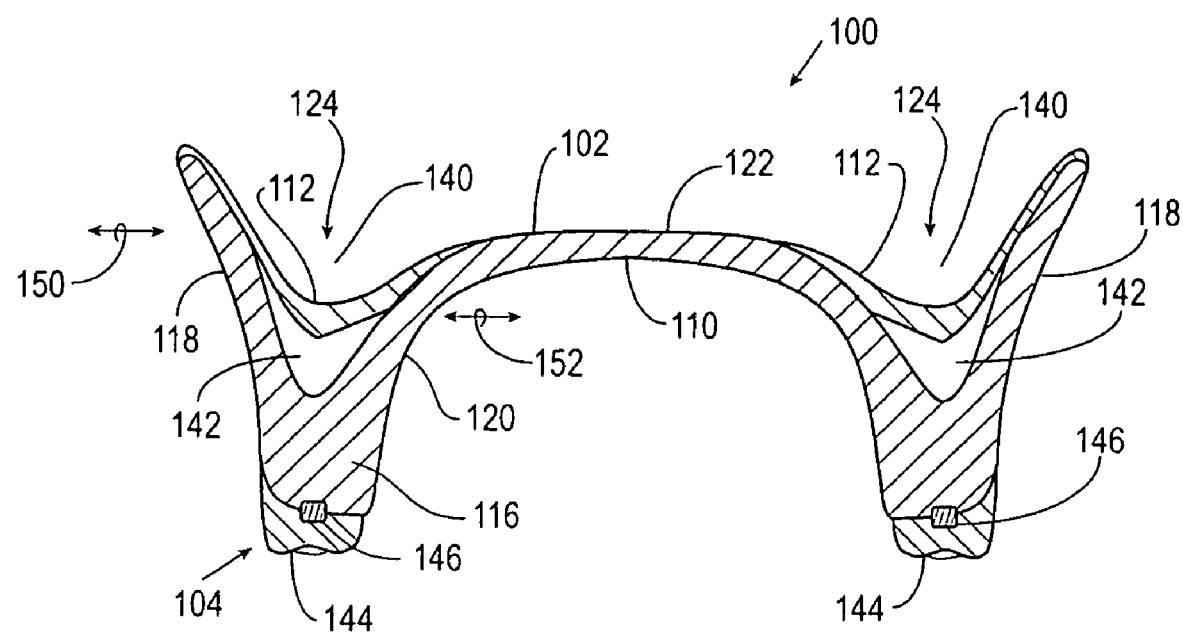
FIG. 14 is another cross-sectional view of the denture depicted in FIG. 10, taken along the lines 14-14 of FIG. 11.
Figure 15:
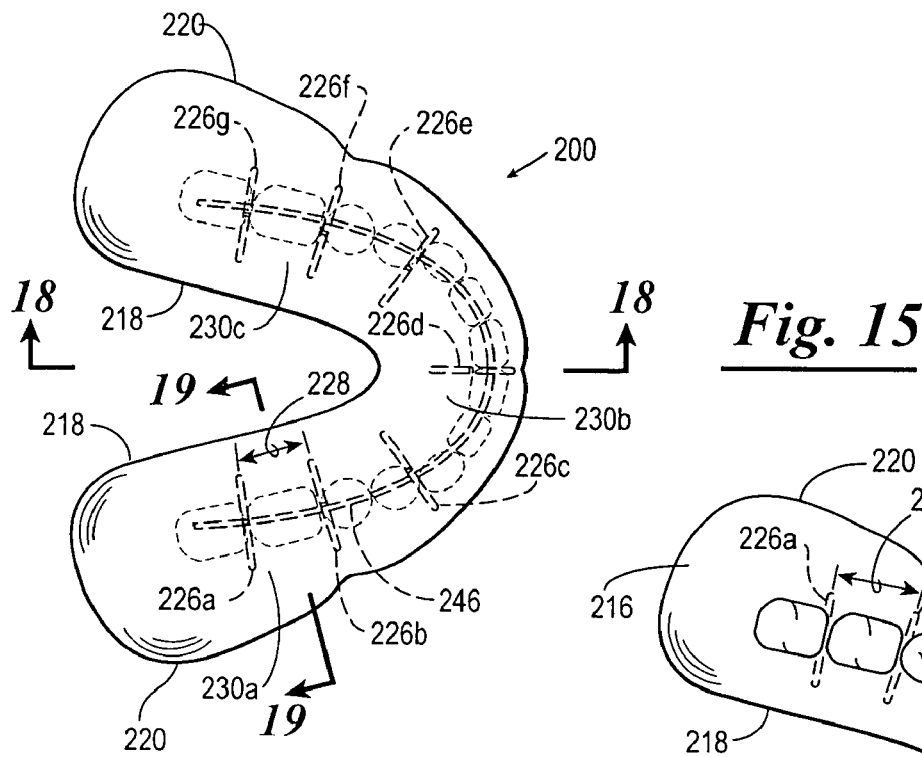
FIG. 15 is another example of a denture constructed in accordance with the present invention.
Figure 16:
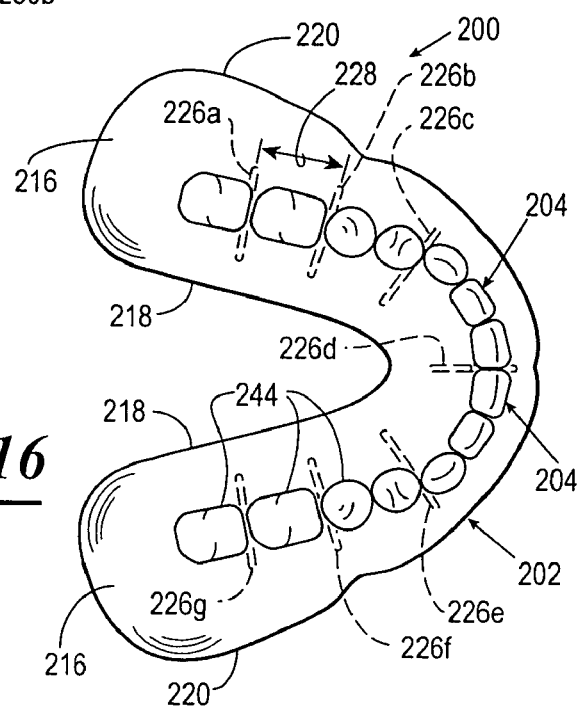
FIG. 16 is a top plan view of the denture depicted in FIG. 15.
Figure 17:
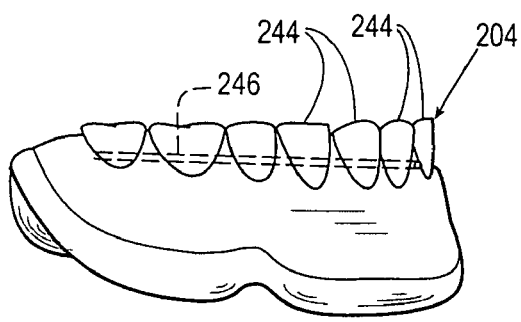
FIG. 17 is a side elevational view of the denture depicted in FIG. 15.
Figure 18:
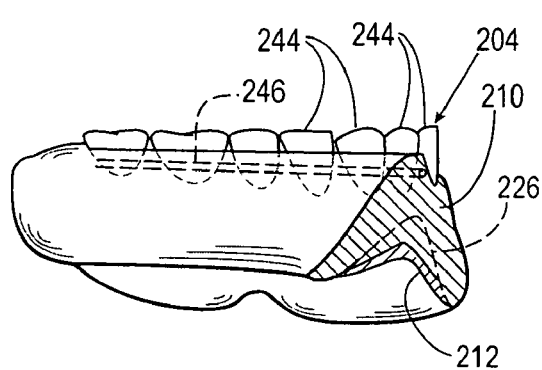
FIG. 18 is a cross-sectional view of the denture depicted in FIG. 15, taken along the lines 18-18 of FIG. 15.

The deformable member 112 is positioned across the channel 124 so as to divide or separate the channel 124 into a gum receiving section 140 (FIG. 14), and a fitting section 142. As best shown in FIG. 14, the deformable member 112 is preferably constructed of a material which is connected to the labial wall 120, and the lingual wall 118. However, it should be understood that the deformable member 112 could also be connected to the palate portion 122 if desired. Further, when the deformable member 112 is connected to the palate portion 122, then connection of the deformable member 112 to the lingual wall 118 is optional.

In general, the gum receiving section 140 is sized and shaped so as to receive a portion of the patient's gum, while the fitting section 142 of the channel 124 is sized and shape so as to provide clearance for the deformable member 122 to move into the fitting section 142 so that the gum receiving section of the channel 124 conforms to the patient's gum.

The deformable member 112 can be constructed of one or more materials which are soft and pliable as discussed herein. Preferably, the deformable member 112 is relatively more soft and pliable than the one or more materials forming the support member 110. It should be understood that the support member 110 and the deformable member 112 cooperate to provide a fitting state and a non-fitting state of the denture plate 102. In the fitting state, the deformable member 112, and at least the ridges 126 of the support member 110 are capable of being reshaped to conform the gum receiving section of the channel 124 to conform to the gum of the patient. In one version, the entire support member 110 and deformable member 112 can be reshaped in the fitting state. In the non-fitting state, the deformable member 112, and also preferably the support member 110 are both soft and pliable but have a memory to remain fitted to the patient's gum. Thus, as shown by the arrows 150 and 152, the lingual wall 118, and the labial wall 120 can be adjusted slightly so as to release from the patient's gum and/or to be positioned on to the patient's gum, but the memory of the lingual wall 118, and the labial wall 120 in the non-fitting state still remain fitted to closely conform to the patient's gum while being worn.

By way of example, the support and deformable members 110 and 112 could be manufactured by compression molding, thermo-forming, plastic machining, injection molding, or other methods of forming and shaping polymeric material. The decision on which method to use is often related to material selection of the base and the quantity of the base to be manufactured. Additionally, due to the deformable nature of the material, some methods may be more advantageous than others. The preferred manufacturing method would allow for a strong bond between the deformable material and the base material.

Stereolithography could be employed in a situation where one or more custom deformable members 112 are desired. An impression would be taken of the patient's mouth. The impression would be used to form a model of the mouth. The impression could then be laser scanned resulting in a 3-D Computer Aided Design (CAD) model. The CAD model for the custom deformable members could then be manipulated by a variety of means to result in a computer model suitable to work from to create physical components. Also, the deformable members could be created in 3-dimensional CAD software. The ultimate result of the CAD modeling process would be a file that could be used to create physical models by plastic molding techniques.

In the case of stereolithography, the resulting model might be of the mold used to create a patient's custom deformable members. Then, when the stereolithography apparatus (SLA) model is complete, it is used as a sacrificial item to create the deformable members from a suitable material.

The stereolithography (or SLA) process is simply an example of the many types of rapid manufacturing or rapid prototyping methods. Other examples include, but are not limited to, Selective Laser Sintering (SLS), wax printing, and fused deposition modeling (FDM).

The false teeth assembly 104 is attached to the support member 110 of the denture plate 102 at the base 116. The false teeth assembly 104 is provided with a plurality of false teeth 144 connected together with a reinforcing bar 146. The false teeth 144 can be made of porcelain, acrylic, plastic, or the like. The false teeth assembly 104 can be bonded to the base 116 of the denture plate 102 chemically, but it is preferable that the false teeth 144 be bonded to the base 116 of the denture 102 mechanically. In one embodiment, holes are drilled through the false teeth 144 so that upon connecting the false teeth 144 to the base 116, the material forming the base 116 flows through the holes upon curing to form the mechanical bond. The teeth can also be screwed on, clipped to, or snapped onto the base 116 of the denture palate 102. The reinforcing bar 146 can be made of any material; such as but not limited to, metal, plastic, rubber, etc. The reinforcing bar 146 may be embedded in the denture plate and/or the false teeth 144. The reinforcing bar 146 is shown to be in the middle of the false teeth 144; on the other hand, the reinforcing bar 146 does not need to be positioned in the middle of the false teeth 144. The reinforcing bar 146 can be positioned next to a chewing surface of the false teeth 144 in order to assist in chewing the food. The reinforcing bar 146 may be positioned in a lower portion of the false teeth 144 close to the base 116 in order to provide better bonding between the false teeth 144 and the base 116. In addition, multiple reinforcing bars 146 may be used to connect the false teeth 144, in which the reinforcing bars 146 may be positioned in the same or different areas of the false teeth 146. For example, a reinforcing bar 146 can be positioned next to the chewing surface of the false teeth 144 and another reinforcing bar 146 can be positioned close to the base 116.

Additionally, the false teeth assembly 104 could be manufactured by compression molding, thermo-forming, plastic machining, injection molding, or other methods of forming and shaping polymeric material. The decision on which method to use is often related to the material selection of the false teeth and the quantity of false teeth to be manufactured. Additionally, the inclusion of the reinforcing bar 146 often impacts which method one might choose. Thus, the preferred method is a process whereby the plastic material is adhered to the reinforcing bar during the false teeth assembly forming process.

Stereolithography could be employed in a situation where a custom false teeth assembly 104 is desired. An impression would be taken of the patient's existing teeth. The impression would be used to form a model of the teeth. Either the impression or the model could then be laser scanned resulting in a 3-D Computer Aided Design (CAD) model. The CAD model for the custom set of teeth could then be manipulated by a variety of means to result in a computer model suitable to work from to create physical components. One example would be to mirror any of the patient's missing teeth from one side of the mouth to the other if teeth are intact on the opposite side of the mouth. Also, the false teeth assembly 104 could be created in 3-dimensional CAD software. The ultimate result of the CAD modeling process would be a file that could be used to create physical models by processes such as precision machining or stereolithography.

In the case of stereolithography, the resulting model might be of the mold used to create a patient's custom set of teeth. Then, when the stereolithography apparatus (SLA) model is complete, it is used as a sacrificial item to create the false teeth from a suitable material.

The stereolithography (or SLA) process is simply an example of the many types of rapid manufacturing or rapid prototyping methods. Other examples include, but are not limited to, Selective Laser Sintering (SLS), wax printing, and fused deposition modeling (FDM).

Referring now to FIGS. 15-19, shown therein and designed by a reference numeral 200 is another example of a denture constructed in accordance with the present invention. FIGS. 15-19 show a "lower" denture 200, which similar to the denture 50 of FIG. 2, is intended for use as a "lower" denture. As well known in the art, the "lower" denture is intended for use with the lower portion of a patient's mouth. The denture 200 is similar to the denture 100 in all its components; except that the "lower" denture does not have a palate portion 122 as in the "upper" denture 100. Note that the similar components of the denture 200 shown in FIGS. 15-19 are numbered identically as the corresponding components in the denture 100 shown in FIGS. 10-14, but using a 200 series of numbers rather than the 100 series. Therefore, the denture 200 would be understood to generally include a denture plate 202 and a false teeth assembly 204, the denture plate 202 being provided with a support member 210 and a deformable member 212 constructed of soft and pliable materials. The support member 210 is provided with a base 216, a lingual wall 218, and a labial wall 220. The support member 210 is further provided with a plurality of ridges 226 (designated by reference numerals 226a-226g) being spatially disposed from an adjacently positioned ridge 226 to form the gaps 230 (designated by reference numerals 230a-230c). Further, the false teeth assembly 204 is provided with a plurality of false teeth 244 connected together with a reinforcing bar 246.

Figure 19:
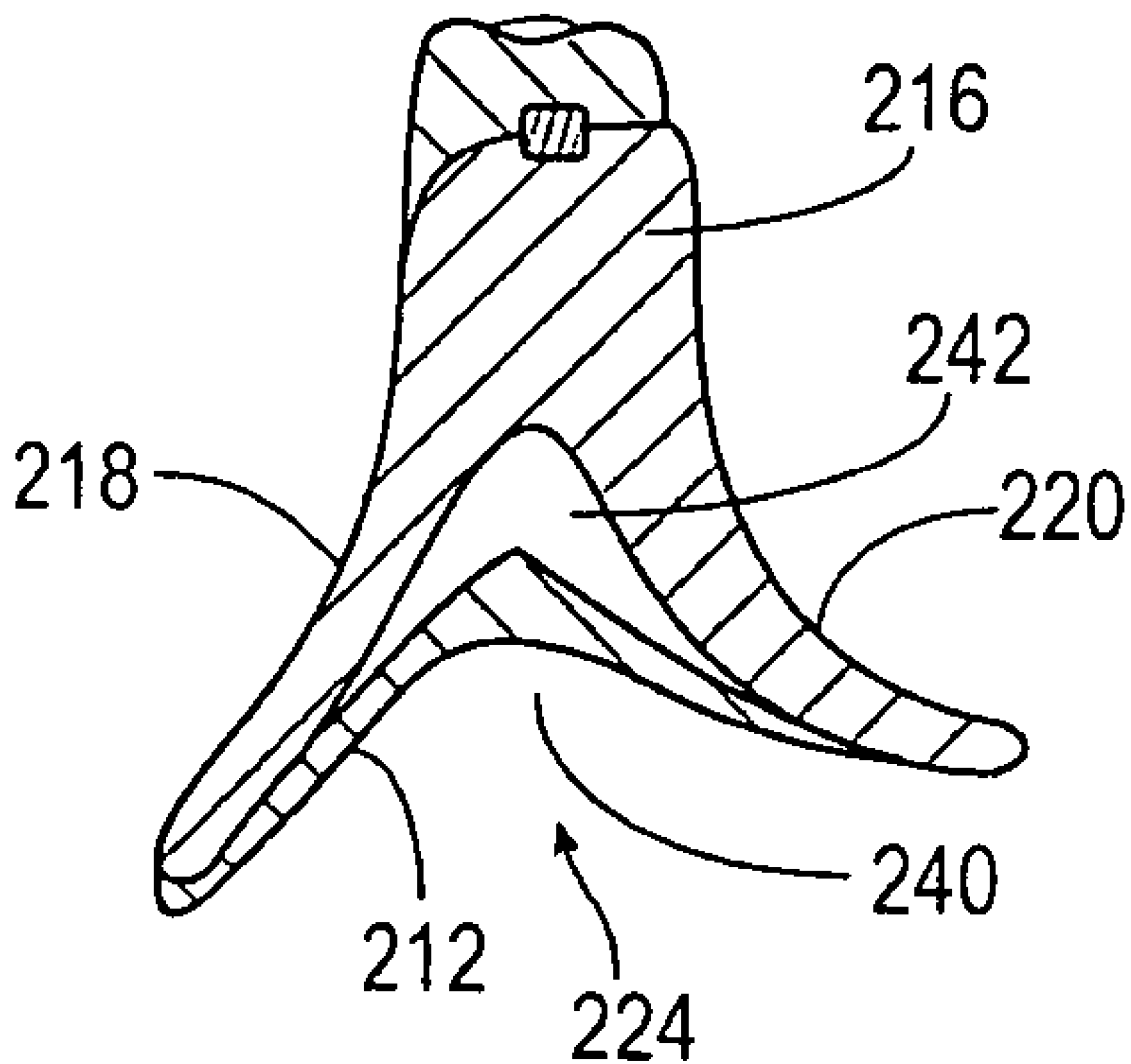
FIG. 19 is another cross-sectional view of the denture depicted in FIG. 15, taken along the lines 19-19 of FIG. 15.

Unlike the base 116 of the "upper" denture 100, the base of the "lower" denture 200 faces up, towards the "upper" denture or the "upper" jaw of a patient's mouth. Yet, a base 216, a lingual wall 218, and a labial wall 220 together form a channel 224, as shown in FIG. 19. The channel 224 is bisected by a deformable member 212, thus, forming a gum receiving section 240 and a fitting section 242. Since the base 216 of the "lower" denture 200 is 180 degree flip image of the base 116 of the "upper" denture 100, the channel 224, the gum receiving section 240, and the fitting section 242 also face the opposite direction of the channel 114, the gum receiving section 140, and the fitting section 142 of the "upper" denture 100.

Both the "upper" denture 100 and the "lower" denture 200 can be made in different sizes and shapes, without the need of an impression of a specific patient's mouth. Therefore, both the "upper" denture 100 and the "lower' denture 200 can be mass produced or pre-made. Both dentures can also be fitted to a specific patient's mouth after they are molded. It should also be noted that a patient may or may not be a human. In other words, a patient using the "upper" denture 100 or the "lower" denture 200 may be an animal, such as, a cat, a dog, a sheep, or the like.

In general, a denture can be manufactured using compression molding, thermo-forming, stereolithography, vacuum forming, plastic machining, or injection molding. Even though the preferred method of manufacturing is Plastic Injection Molding, the "upper" denture 100 and the "lower" denture 200 can be manufactured using any of the above mentioned manufacturing methods as long as the resulting denture is a soft, pliable denture that can be reshaped to fit a patient's mouth after the denture has been manufactured or molded.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification.

What is claimed is:

1. A denture comprising:
   a denture plate comprising:
      a support member having an approximately U-shape base, a labial wall extending from said base and a lingual wall extending from said base; said base, labial wall and lingual wall forming an approximate U-shape cross-section along an imaginary vertical plane to form a channel; and
      a deformable member extending across the channel and spaced a distance from the U-shape base to separate the channel into a gum receiving section and a filling section, the fitting section includes a plurality of ridges extending between the U-shape base and the deformable member, wherein the deformable member is constructed of soft and pliable material; and,
   a false teeth assembly including a plurality of false teeth secured to said base, wherein the false teeth assembly includes a reinforcing bar embedded within and connecting the plurality of false teeth.

2. The denture of claim 1 wherein the support member is constructed of a soft, pliable material.

3. The denture of claim 2 wherein the soft, pliable material forming the support member is firmer than the soft pliable material forming the deformable member.

4. The denture of claim 3 wherein the soft, pliable materials forming the support member and the deformable member can be heated into a fitting state.

5. The denture of claim 4 wherein the denture is pressed against the gums of a patient while in the fitting state and thereby adopts the shape of the patient's gums.

6. The denture of claim 5 wherein the soft, pliable material forming the support member and the deformable member retains the shape of the patient's gums while in a non-fitting state.

7. The denture of claim 1 wherein the ridges are made of firmer material than the deformable member.

8. The denture of claim 1 wherein the false teeth are manufactured using an operation selected from the group consisting of: a machining operation, a compression molding operation, an injection molding operation, a vacuum forming operation, a stereolithography operation, a rapid prototyping technique, and combinations thereof.

9. The denture of claim 1 wherein the support member is manufactured using an operation selected from the group consisting of: a machining operation, a compression molding operation, an injection molding operation, a vacuum forming operation, a stereolithography operation, a rapid prototyping technique, and combinations thereof.

10. The denture of claim 1 wherein the deformable member is manufactured using an operation selected from the group consisting of: a machining operation, a compression molding operation, an injection molding operation, a vacuum forming operation, a stereolithography operation, a rapid prototyping technique, and combinations thereof.

11. The denture of claim 1 wherein the deformable member is constructed of ethyl vinyl acetate.

\* \* \* \* \*